US010904388B2

(12) United States Patent
Ravi et al.

(10) Patent No.: US 10,904,388 B2
(45) Date of Patent: Jan. 26, 2021

(54) REPRIORITIZING WAITLISTED CALLERS BASED ON REAL-TIME BIOMETRIC FEEDBACK

(71) Applicant: International Business Machines Corporation, Armonk, NY (US)

(72) Inventors: Manjunath Ravi, Austin, TX (US); Su Liu, Austin, TX (US); Kai Liu, Malden, MA (US); Zhichao Li, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 100 days.

(21) Appl. No.: 16/137,623

(22) Filed: Sep. 21, 2018

(65) Prior Publication Data
US 2020/0099791 A1 Mar. 26, 2020

(51) Int. Cl.
*H04M 3/523* (2006.01)
*H04M 3/51* (2006.01)
(Continued)

(52) U.S. Cl.
CPC ......... *H04M 3/5235* (2013.01); *A61B 5/0022* (2013.01); *A61B 5/02055* (2013.01); *A61B 5/14532* (2013.01); *A61B 5/163* (2017.08); *A61B 5/165* (2013.01); *A61B 5/443* (2013.01); *A61B 5/4875* (2013.01);
(Continued)

(58) Field of Classification Search
CPC .. H04M 3/5232; H04M 3/5238; H04M 3/436; H04M 2203/554; H04M 3/5235; H04M 3/5175; H04M 3/4938; H04M 2201/405; A61B 6/165; A61B 5/163; A61B 5/02055; A61B 5/443; A61B 5/4875; A61B 5/14532; A61B 5/0022; A61B 5/4884; A61B 55/021; A61B 5/024
See application file for complete search history.

(56) References Cited

U.S. PATENT DOCUMENTS 6,485,416 B1 11/2002 Platt et al.
7,013,005 B2 * 3/2006 Yacoub ................. H04M 3/523
379/265.13
(Continued)

FOREIGN PATENT DOCUMENTS

CN 102866843 A 1/2013
WO 2005096613 A1 10/2005

OTHER PUBLICATIONS

IBM; "WebSphere Voice Response for AIX with Direct Talk Technology—General Information and Planning"; IBM Corporation, www.ibm.com/GC34-7084-09 <http://www.ibm.com/GC34-7084-09>; Version 6.1; 2014.
(Continued)

*Primary Examiner* — Lisa Hashem
(74) *Attorney, Agent, or Firm* — Patterson + Sheridan, LLP (57) ABSTRACT

Techniques for reprioritizing waitlisted callers using biometric feedback. A biometric aspect of a calling user is monitored in real time via a sensor. A digital output characterizing an emotional state of the user is generated. The digital output is encoded and transmitted to a server via multi-frequency signaling. The server decodes the digital output and reprioritizes the calling user relative to other calling users in the waitlist, in order to expedite the calling user being serviced.

20 Claims, 6 Drawing Sheets

(51) Int. Cl.
*H04M 3/493* (2006.01)
*A61B 5/16* (2006.01)
*A61B 5/0205* (2006.01)
*A61B 5/00* (2006.01)
*A61B 5/145* (2006.01)
*A61B 5/021* (2006.01)
*A61B 5/024* (2006.01)

(52) U.S. Cl.
CPC ......... *A61B 5/4884* (2013.01); *H04M 3/4938* (2013.01); *H04M 3/5175* (2013.01); *A61B 5/021* (2013.01); *A61B 5/024* (2013.01); *H04M 2201/405* (2013.01)

(56) References Cited

U.S. PATENT DOCUMENTS

| | | | |
|---|---|---|---|
| 7,136,475 B1 | 11/2006 | Rogers et al. | |
| 7,684,556 B1* | 3/2010 | Jaiswal | H04M 3/5166 379/266.01 |
| 7,986,716 B2 | 7/2011 | Veeramachaneni et al. | |
| 8,521,536 B1 | 8/2013 | Fox | |
| 9,537,924 B2* | 1/2017 | Barnett | G06F 3/04842 |
| 10,448,887 B2* | 10/2019 | Danson | A61B 5/0531 |
| 2003/0108162 A1* | 6/2003 | Brown | H04M 1/575 379/88.01 |
| 2004/0022384 A1* | 2/2004 | Flores | H04M 3/38 379/265.13 |
| 2007/0121824 A1* | 5/2007 | Agapi | H04M 3/5175 379/88.18 |
| 2008/0192736 A1 | 8/2008 | Jabri et al. | |
| 2008/0205624 A1* | 8/2008 | Mandalia | H04M 3/51 379/265.02 |
| 2010/0278318 A1* | 11/2010 | Flockhart | H04M 3/51 379/88.04 |
| 2014/0205077 A1* | 7/2014 | Wood | H04M 3/42042 379/142.01 |
| 2019/0109943 A1* | 4/2019 | Harris | H04W 12/06 |
| 2020/0045179 A1* | 2/2020 | Firpo | H04M 3/436 |
| 2020/0106882 A1* | 4/2020 | Fang | G06Q 30/016 |

OTHER PUBLICATIONS

Commarford, P.; "Working Memory, Search and Signal Detection: Implications for Interactive Voice Response System Menu Design"; Doctoral Dissertation, University of Central Florida; 2006.

Anonymously; "Method and Apparatus to Manage Call-ins for a Mobile"; <http://ip.com/IPCOM/000215263D>; Feb. 23, 2012.

Motorola et al.; "Requesting the Call Subject and/or Call Priority based on Callee Preferences and Converting it into Text/Multimedia to Present to Callee"; <http://ip.com/IPCOM/000140990D>; Sep. 28, 2006.

Anonymously; "System and Method for Non-Sequential Access in Telephony Voice Applications"; <http://ip.com/IPCOM/000235420D>; Aug. 26, 2014.

"DTMF Generator for Binary Coded Hexadecimal Data" EFG7189 and EFG71891, SGS-Thompson Microelectronics, Jul. 1993, 13 pp. http://pe2bz.philpem.me.uk/pdf%20on%20typenumber/D-H/EFG7189.pdf.

GitHub—palmerc/DTMFSounds: Swift DTMF tone generation, viewed Sep. 20, 2018, 1 pp. https://github.com/palmerc/DTMFSounds.

GitHub—Generate DTMF tones, viewed Sep. 20, 2018, 1 pp. https://gist.github.com/jamesu/3296747.

Lesson 2—Adding DTMF Input, Microsoft Docs, Mar. 25, 2013, 11 pp., viewed Sep. 20, 2018; https://msdn.microsoft.com/en-us/library/ff769502.aspx.

GitHub—codyaray/dtmf-signaling: A MATLAB program to encode and decode the dual-tone multiple-frequency (DTMF) signals used to dial a telephone, 2018, viewed Sep. 20, 2018, https://github.com/codyaray/dtmf-signaling.

Generate DTMF Tones, StackOverflow, viewed Sep. 20, 2018 https://stackoverflow.com/questions/1399501/generate-dtmf-tones#.

* cited by examiner

| # | KEY SEQUENCE | MULTI-FREQUENCY SEQUENCE (Hz) |
|---|---|---|
| 1 | 1 | 697 & 1209 |
| 2 | 2 | 697 & 1336 |
| 3 | 3 | 697 & 1477 |
| 4 | 4 | 770 & 1209 |
| 5 | 5 | 770 & 1336 |
| 15 | #, 3 | 941 & 1477, 697 & 1477 |
| 16 | #, 4 | 941 & 1477, 770 & 1209 |
| 17 | #, 5 | 941 & 1477, 770 & 1336 |

REPRIORITIZING WAITLISTED CALLERS BASED ON REAL-TIME BIOMETRIC FEEDBACK

BACKGROUND

Embodiments presented in this disclosure relate to call center management techniques. More specifically, embodiments disclosed herein relate to techniques for reprioritizing waitlisted callers based on real-time biometric feedback.

For many businesses, call centers play increasingly important roles in providing superior customer service in a cost-effective manner. Call centers enable businesses to offer their customers products, services and customer support twenty-four hours a day, seven days a week. Sophisticated switching equipment and software for call centers provide Automatic Call Distribution (ACD) capabilities, enabling customer calls to be routed efficiently to agents in the call center who have the appropriate skills to handle the customers' specific requirements. The software keeps records of calls in order to track customer needs and preferences, manage agent states and activities, and maintain statistics on agent performance. The software also balances the load of incoming calls from customers among the available agents, using data provided by the switching equipment, to maximize the efficiency of use of call center resources and to minimize customer waiting time.

SUMMARY

One embodiment includes a computer-implemented method of biometric monitoring to reprioritize calling users in a queue. The computer-implemented method includes monitoring, via a sensor in real time, a biometric aspect of a calling user when the calling user is on hold during a customer service call having an associated queue, wherein the customer service call and the queue are managed by a server. The computer-implemented method also includes generating, based on the biometric aspect of the calling user, a digital output characterizing an emotional state of the user, where the emotional state includes an unfavorable emotional state. The computer-implemented method also includes encoding, by operation of one or more computer processors of a mobile device of the user, the digital output characterizing the emotional state of the user. The computer-implemented method also includes transmitting the encoded digital output to the server via multi-frequency signaling, whereupon the server decodes the digital output and reprioritizes the calling user relative to other calling users in the queue based on the unfavorable emotional state, in order to expedite the calling user being serviced.

Another embodiment includes a computer program product of biometric monitoring to reprioritize calling users in a queue. The computer program product includes a computer-readable storage medium having computer readable program code embodied therewith. The computer readable program code is executable by one or more computer processors to perform an operation that includes monitoring, via a sensor in real time, a biometric aspect of a calling user when the calling user is on hold during a customer service call having an associated queue, where the customer service call and the queue are managed by a server. The operation also includes generating, based on the biometric aspect of the calling user, a digital output characterizing an emotional state of the user, where the emotional state includes an unfavorable emotional state. The operation also includes encoding the digital output characterizing the emotional state of the user. The operation also includes transmitting the encoded digital output to the server via multi-frequency signaling, whereupon the server decodes the digital output and reprioritizes the calling user relative to other calling users in the queue based on the unfavorable emotional state, in order to expedite the calling user being serviced.

Still another embodiment includes a system of biometric monitoring to reprioritize calling users in a queue. The system includes one or more computer processors and a memory program a program which, when executed by one or more computer processors, performs an operation that includes monitoring, via a sensor in real time, a biometric aspect of a calling user when the calling user is on hold during a customer service call having an associated queue, where the customer service call and the queue are managed by a server. The operation also includes generating, based on the biometric aspect of the calling user, a digital output characterizing an emotional state of the user, where the emotional state includes an unfavorable emotional state. The operation also includes encoding the digital output characterizing the emotional state of the user. The operation also includes transmitting the encoded digital output to the server via multi-frequency signaling, whereupon the server decodes the digital output and reprioritizes the calling user relative to other calling users in the queue based on the unfavorable emotional state, in order to expedite the calling user being serviced.

DETAILED DESCRIPTION

Embodiments presented in this disclosure provide techniques for reprioritizing waitlisted callers based on real-time biometric feedback. Doing so can permit a call center operator to manage the ordering of waitlisted callers in a manner that more accurately reflects the relative urgency or severity of the need of each waitlisted caller to be serviced by a customer support representative.

Figure 1:
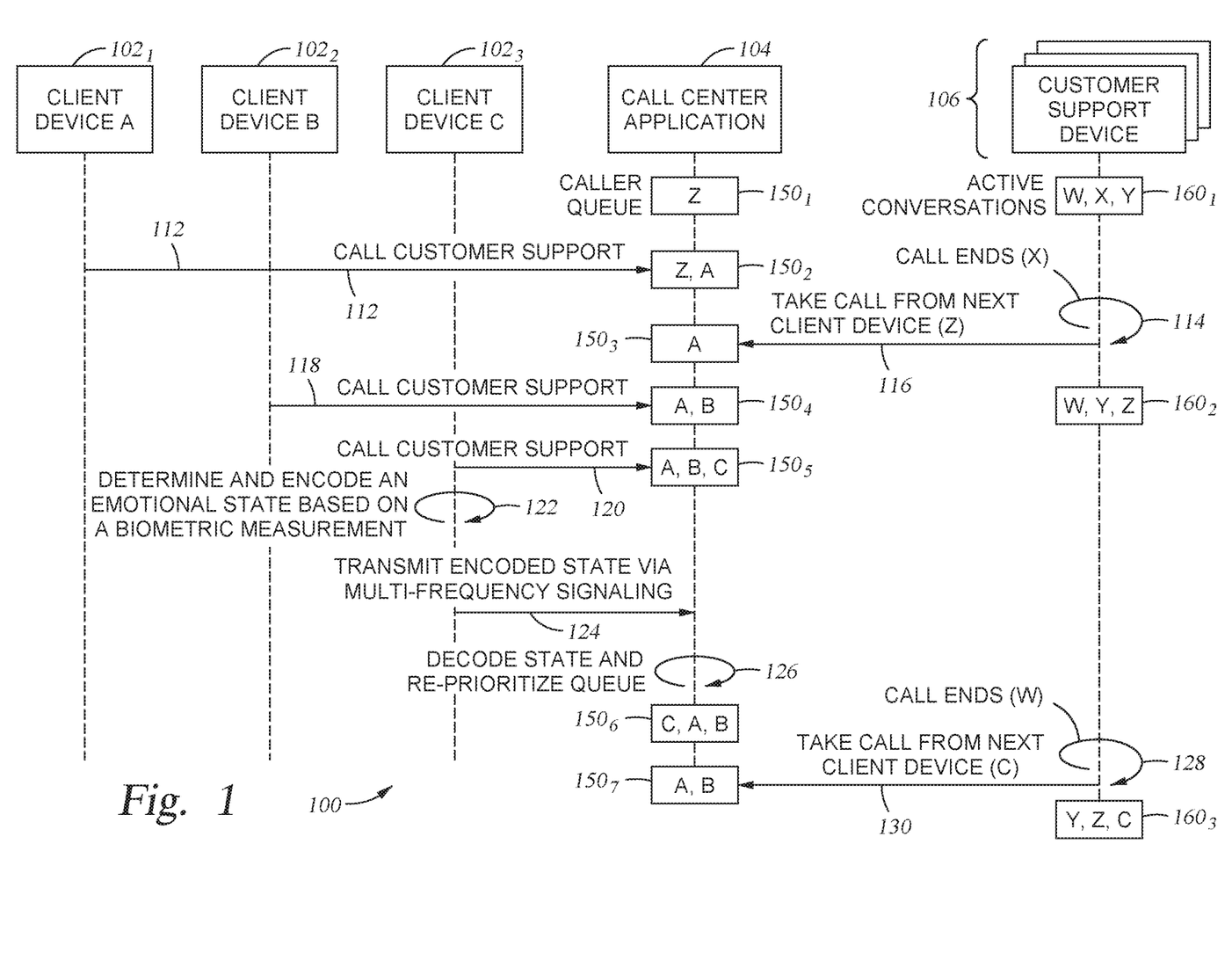
FIG. 1 is a sequence diagram for reprioritizing waitlisted callers based on real-time biometric feedback, according to one embodiment presented in this disclosure.

FIG. 1 is a sequence diagram 100 for reprioritizing waitlisted callers based on real-time biometric feedback, according to one embodiment presented in this disclosure. The sequence diagram 100 indicates that customer support devices 106 permit customer support representatives to engage in dialogue with calling users, the calling users having client devices $102_{1-3}$. As used herein, dialogues or conversations between customer support representatives and calling users can be conducted in any format, including text, audio, and/or video, and via any medium of exchange including telephony, electronic mail, instant messaging, voice messaging, video conferencing, etc. Customer support representatives are also referred to herein as customer service representatives or customer service agents.

At least in some embodiments, the interactions between the customer support representatives and the calling users are monitored and/or managed by a call center application 104. The call center application can be operatively connected with the client devices $102_{1-3}$ and/or the customer support devices 106. Additionally or alternatively, the call center application 104 can be operatively connected with one or more intermediary devices configured to provide the call center application 104 with real-time metrics regarding the interactions between the customer support representatives and the calling users.

In one embodiment, the call center application 104 can maintain data structures for use in managing the interactions. The data structures include a caller queue $150_{1-7}$ of calling users, and active conversations $160_{1-3}$ between the calling users and the customer support representatives via the client devices $102_{1-3}$ and/or the customer support devices 106. The caller queue is also referred to herein as a queue. The data structures may also include a roster of customer support representatives, the roster indicating, at any point in time, which customer support representatives are on or off duty, and (if on duty) are available or occupied. In this regard, the roster can be updated in real time by the call center application 104 responsive to the customer support representatives logging in or out of their customer support representative accounts via a call center client interface on their customer support devices 106.

In some embodiments, when a calling user calls the call center, the call center application 104 determines whether any customer support representative is available to converse with the calling user. If a customer support representative is available, the call center application 104 can assign the customer support representative to converse the calling user, in which case the call center application 104 updates the data structure of active conversations to include the conversation between the calling user and the customer support representative. Where multiple customer support representatives are available, the call center application 104 can select a customer support representative to assign to the calling user, based on a first predefined selection scheme, such as round-robin selection or random/pseudorandom selection. Users in the queue are de-queued according to a second predefined selection scheme. The second predefined selection scheme can be a variant of first-in, first-out that permits reprioritization based on real-time biometric feedback, according to the embodiments disclosed herein.

If no customer support representative is available but at least one customer support representative is on duty, the calling user is put on hold to await customer support representative availability, in which case the call center application 104 updates the queue to include the calling user. In some embodiments, in addition to or as an alternative to putting the calling user on hold, the call center application 104 can cause the calling user to be presented with an option of receiving a return call from a customer support representative once the customer support representative becomes available. If the calling user opts for the presented option, the calling user can hang up while still remaining in the queue. If no customer support representative is on duty, e.g., the calling user is calling outside of business hours, the calling user is not added to the queue, and the calling user is instructed to call again during business hours.

For instance, assume that there are three customer support representatives on duty at a given point in time. As reflected in active conversations $160_1$, the three customer support representatives are engaged in conversations with three calling users, who are associated with client devices W, X, and Y, respectively. If a fourth calling user calls customer support, the fourth calling user, associated with client device Z, is placed in the queue $150_1$.

As shown, at step 112, another user, associated with client device A $102_1$, calls customer support. Because the active conversations $160_1$ indicate that all three customer support representatives are presently occupied, the call center application 104 updates the queue $150_2$ to include the user associated with client device A $102_1$. At step 114, a conversation ends between the user associated with client device X, and one of the customer support representatives. At step 116, the customer support representative initiates a conversation with the user associated with the client device Z, who is at the front of the queue $150_2$, and the queue $150_3$ is updated to reflect removal of the user associated with the client device Z. The active conversations $160_2$ is also updated to reflect that conversations are currently taking place between the three customer support representatives and the users associated with client devices W, Y, and Z, respectively.

At step 118, yet another user, associated with client device B $102_2$, calls customer support. Because the active conversations $160_2$ indicate that all three customer support representatives are presently occupied, the call center application 104 updates the queue $150_4$ to include the user associated with client device B $102_2$. Similarly, at step 120, still another user, associated with client device C $102_3$, calls customer support. Because the active conversations $160_2$ indicate that all three customer support representatives are presently occupied, the call center application 104 updates the queue $150_5$ to further include the user associated with client device C $102_3$.

At least in some embodiments, designated applications on the client devices $102_{1-3}$, such as call center client applications, can monitor biometric measurements of the calling users to determine emotional states of the users. Depending on the embodiment, the conversations are communicated between the parties over connection established, over a network, by the designated applications or by a communication application separate from the designated applications. The connection can be to the call center application 104 and/or the customer support devices 106, depending on the embodiment. Biometric measurements are also referred to herein as biometric extents or biometric values.

In one embodiment, the biometric measurements can be obtained via one or more sensor modules of the client devices $102_{1-3}$ and/or via one or more sensor devices operatively connected to the client devices $102_{1-3}$. Examples of biometric measurements include those pertaining to heart rate, body temperature, perspiration, hydration level, blood pressure, blood sugar, pupil dilation, and cortisol level.

For instance, at step 122, the designated application on the client device C $102_3$ encodes the determined emotional states, and at step 124, the designated application transmits the encoded emotional states to the call center application 104 in-band via the connection, such as via computer-telephony integration (CTI). In embodiments where the conversation is taking place via telephony, the encoded emotional states can be transmitted to the call center via multi-frequency signaling, e.g., dual-tone multi-frequency signaling. In an alternative embodiment, the encoded emotional states can be at least partially transmitted to the call center application 104 via a separate connection over the same network or via an out-of-band connection over a different network.

At step 126, the call center application 104 decodes the emotional state received from the client device C $102_3$. The call center application 104 then reprioritizes the queue $150_6$ based on the decoded emotional state. For instance, if the decoded emotional state satisfies a predefined reprioritization criterion, such as the user exhibiting a certain measure of unfavorability that satisfies an unfavorability threshold, then the user associated with the client device C $102_3$ can be reprioritized from the back of the queue $150_5$ to the front of the queue $150_6$. For example, the decoded emotional state can indicate that the user is exhibiting a certain level of disapproval or anger while on hold. The unfavorability measure is also referred to herein as an unfavorability level.

Depending on the embodiment, the emotional state can include only an emotional descriptor (e.g., "disapproval"), only a measure of unfavorability (e.g., "7" on a scale from "0" to "10," with "10" representing the most unfavorable), or both the emotional descriptor and the measure of unfavorability. In embodiments where the emotional state only includes an emotional descriptor, the call center application can optionally determine a measure of unfavorability based on a predefined mapping between different emotions and their respective measures of unfavorability. The measure of unfavorability can also be determined based on a biometric mapping that defines a mapping between different types and/or extents of biometric measurements, to different types and/or extents of emotions.

In some embodiments, the user can be reprioritized forward in the queue by a specific extent that is a function of a measure of unfavorability of the decoded emotional state. Depending on the embodiment, specific extent can be represented in terms of a total number of positions in the queue, a percentage of a current capacity or a total capacity of the queue, a total number of positions between the user and the front of the queue, etc.

For instance, if the user exhibits a comparatively higher level of disapproval, the user is reprioritized to the very front of the queue. If the user exhibits a comparatively moderate level of disapproval, the user is reprioritized halfway forward towards the front of the queue, e.g., the user associated with the client device C $102_3$ is reprioritized between the users associated with the client devices A and B $102_{1-2}$, respectively. In some embodiments, if the user exhibits a comparatively lower level of disapproval, the call center application 104 can opt to refrain from reprioritizing the user associated with the client device C $102_3$, thereby leaving the user at the end of the queue $150_5$.

In some embodiments, the encoding and/or transmission of the emotional state by the client device C $102_3$ can be conditioned upon a predefined transmission criterion. In such embodiments, only when the predefined transmission criterion is met is the emotional state encoded and transmitted. Additionally or alternatively, the reprioritization of the queue by the call center application 104 can be conditioned upon the predefined reprioritization criterion as described above. For instance, the client device C $102_3$ can refrain from encoding and transmitting emotional states representing a comparatively lower level of disapproval, as not satisfying an unfavorability threshold specified by the predefined transmission criterion. At least in some embodiments, the predefined transmission criterion and/or the predefined reprioritization criterion can dynamically adjusted over time, such as based on input from an administrative user of the call center application 104, to suit the needs of the call center.

In one embodiment, the predefined transmission criterion and the predefined reprioritization criterion can specify separate unfavorability thresholds, and depending on the embodiment, the thresholds can be the same or different in measure. In a particular embodiment where the thresholds are the same, the call center application 104 reprioritizes the queue $150_6$ based on each emotional state transmitted by the client device C $102_3$ and does not refrain from reprioritizing the queue $150_6$ in any case. In an alternative embodiment where the predefined prioritization criterion specifies a more stringent unfavorability threshold than the predefined transmission criterion, the call center application 104 can refrain from reprioritizing the queue $150_6$ based on a comparatively moderate level of disapproval, as not satisfying the predefined reprioritization criterion, despite the comparatively moderate level of disapproval having satisfied the predefined transmission criterion.

At step 128, a conversation ends between the user associated with client device W, and one of the customer support representatives. At step 130, the customer support representative initiates a conversation with the user associated with the client device C $102_3$, who was reprioritized to the front of the queue $150_6$, and the queue $150_7$ is updated to reflect removal of the user associated with the client device C $102_3$. The active conversations $160_3$ is also updated to reflect that conversations are currently taking place between the three customer support representatives and the users associated with client devices Y, Z, and C, respectively.

Figure 2:
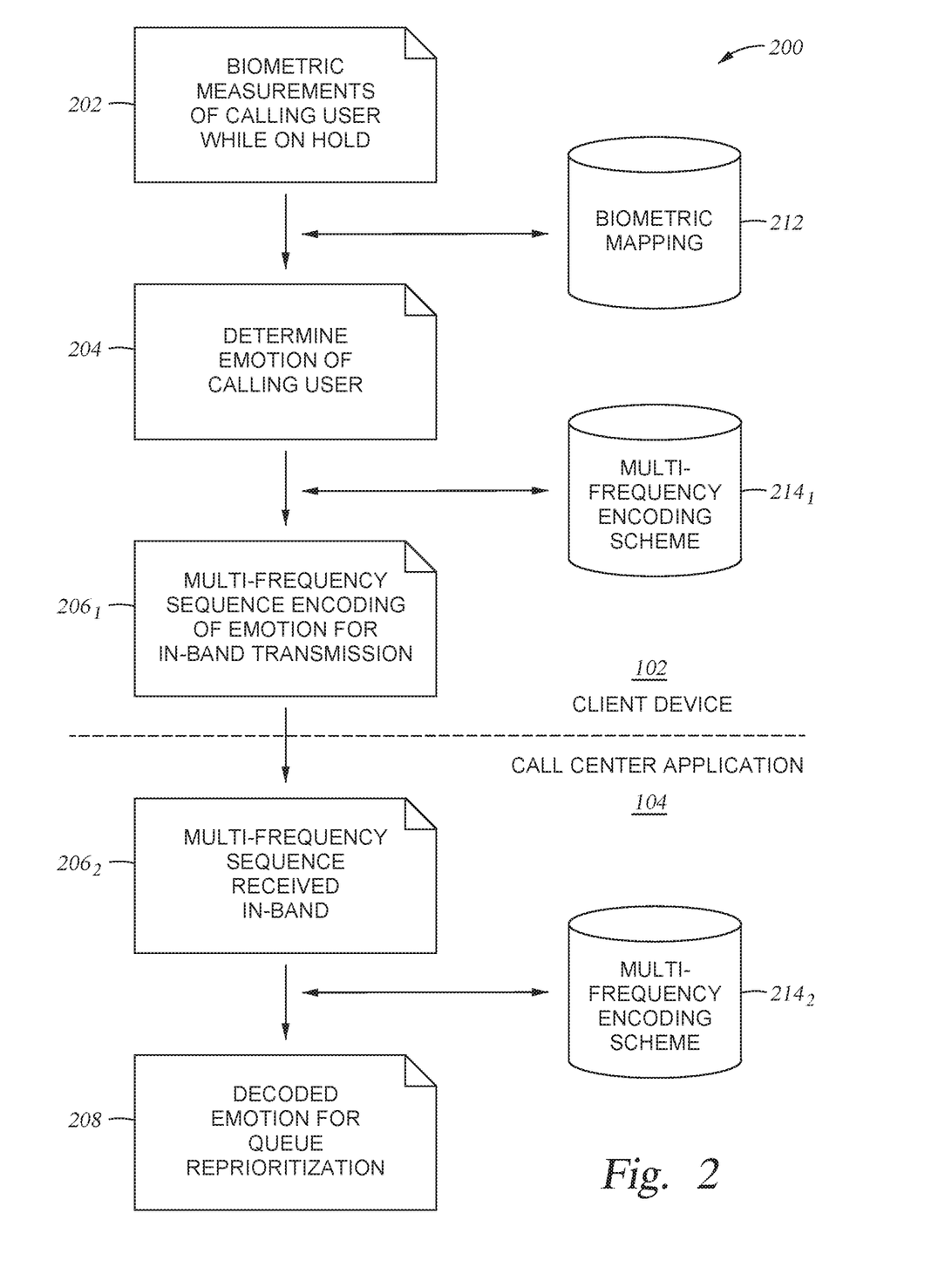
FIG. 2 is a data flow diagram for reprioritizing waitlisted callers based on real-time biometric feedback, according to one embodiment presented in this disclosure.

FIG. 2 is a data flow diagram 200 for reprioritizing waitlisted callers based on real-time biometric feedback, according to one embodiment presented in this disclosure. In one embodiment, the designated application of the client device 102 uses one or more sensors to monitor a calling user while the calling user is on hold, to obtain biometric measurements 202 of the calling user. The designated application generates a determined emotion 204 of the calling user, based on the biometric measurements 202. In some embodiments, the determined emotion 204 is generated based on a biometric mapping 212.

In one embodiment, the designated application generates a multi-frequency sequence $206_1$ that encodes the determined emotion for in-band transmission to the call center application 104. The multi-frequency sequence $206_1$ can be generated based on a multi-frequency encoding scheme $214_1$. In a particular embodiment, the multi-frequency encoding scheme $214_1$ defines how to encode different types and/or extents of emotions into signals for dual-tone multi-frequency transmission. The transmission is received in-band as a multi-frequency sequence $206_2$ by the call center application 104. The call center application 104 next generates a decoded emotion 208 based on the multi-frequency sequence $206_2$. The decoded emotion 208 can be generated based on a multi-frequency encoding scheme $214_2$ corresponding to the one used by the client device 102. The call center application 104 can then reprioritize the queue based on the decoded emotion 208.

Figure 3A:
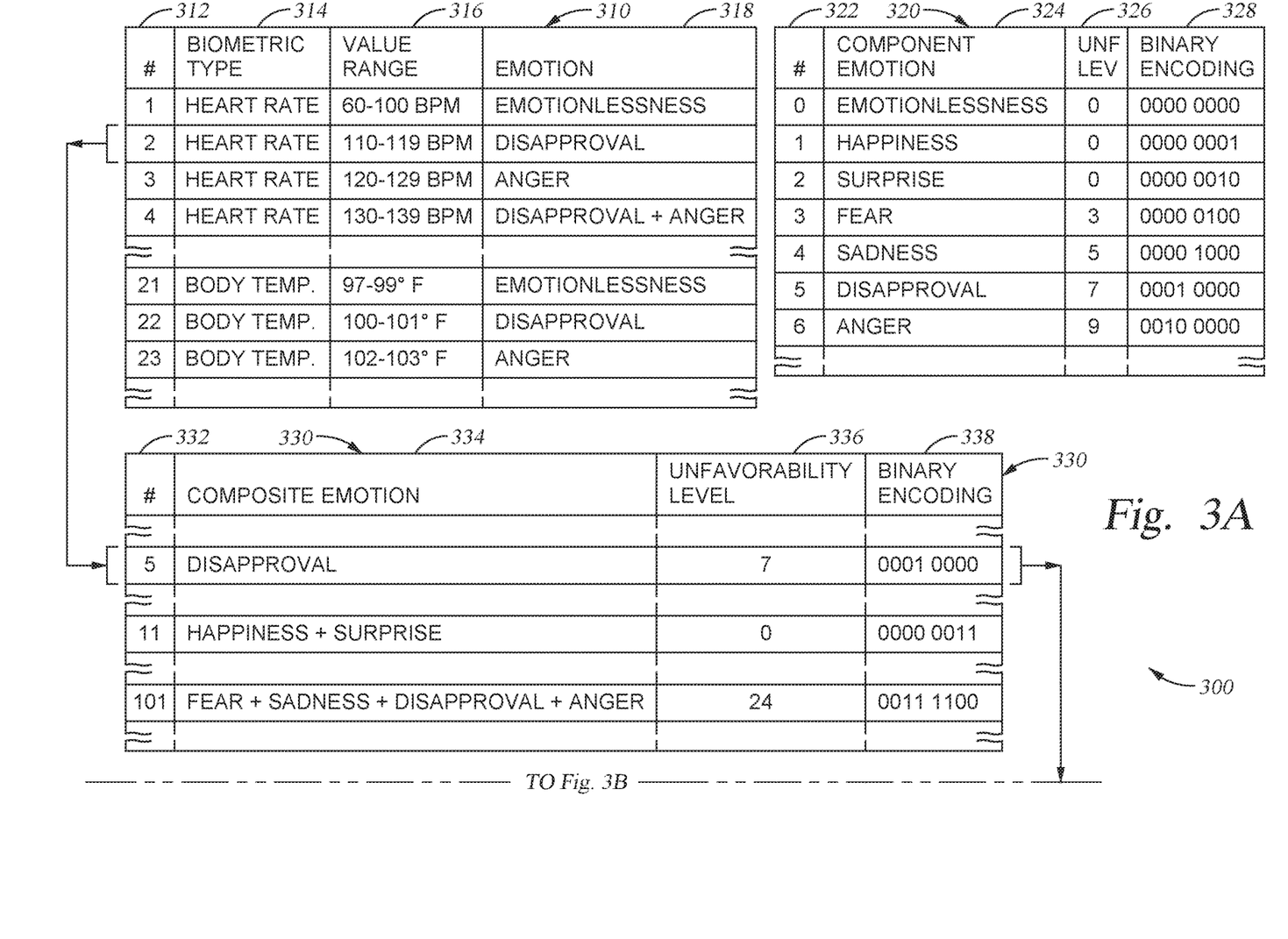
FIGS. 3A-3B depict a block diagram of data structures for reprioritizing waitlisted callers based on real-time biometric feedback, according to one embodiment presented in this disclosure.
Figure 3B:
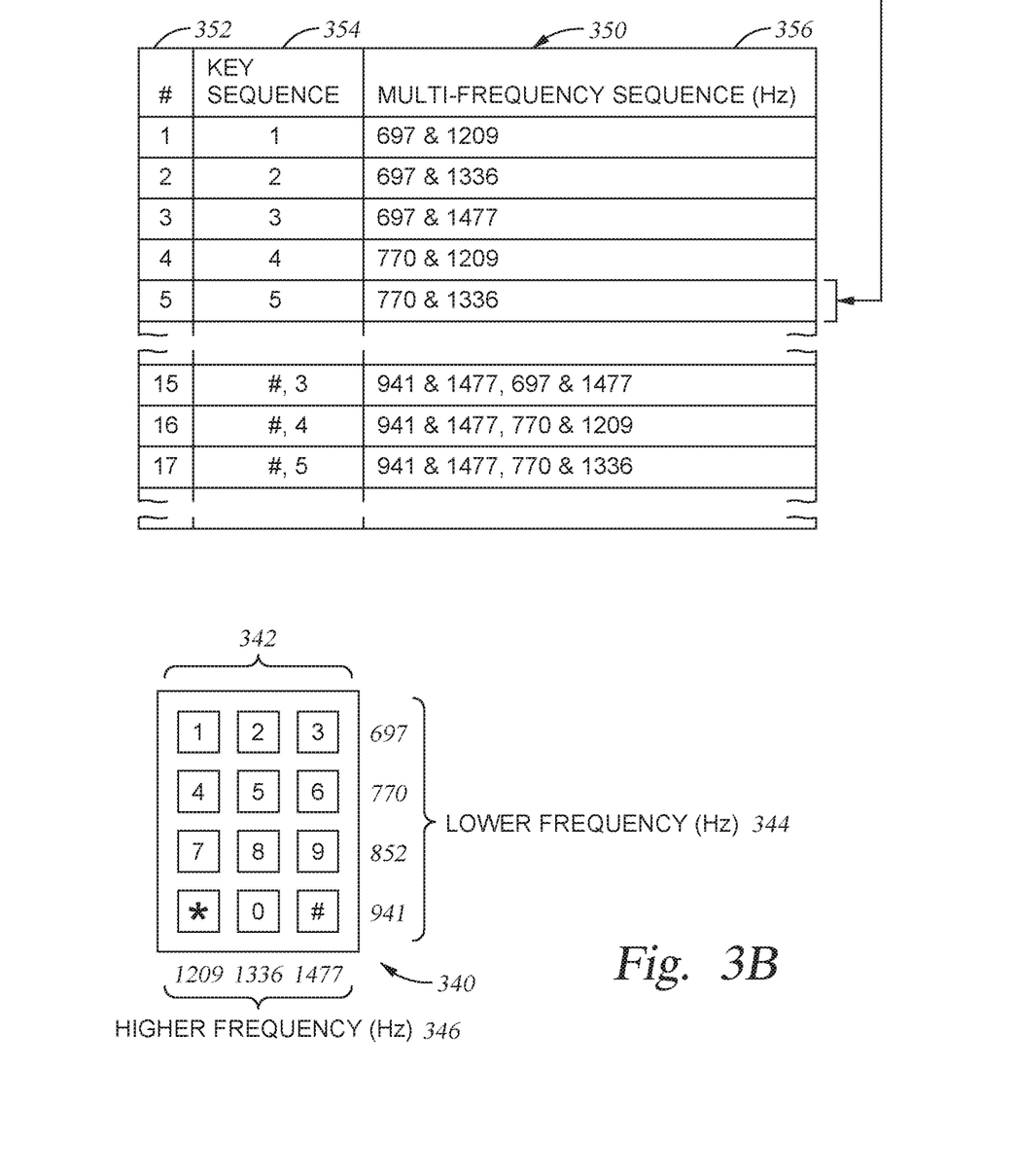

FIGS. 3A-3B depict a block diagram 300 of data structures for reprioritizing waitlisted callers based on real-time biometric feedback, according to one embodiment presented in this disclosure. In some embodiments, the data structures are actually used by the client device 102 and/or the call center application 104 to reprioritize waitlisted callers based on real-time biometric feedback. In alternative embodiments, the client device 102 and/or the call center application 104 reprioritize waitlisted callers based on real-time biometric feedback and by using one or more predefined rules, thereby dynamically performing one or more mappings reflected in the data structures, without actually maintaining any (or some) of the data structures on the computer.

As shown, the data structures include a biometric table 310, a component emotion table 320, and a composite emotion table 330, as shown in FIG. 3A. The data structures further include a frequency map 340 and a sequence table 350, as shown in FIG. 3B.

As shown in FIG. 3A, the biometric table 310 defines mappings between biometric types and value ranges, to corresponding emotions. To that end, the biometric table 310 includes an entry identifier 312, a biometric type 314, a value range 316, and a corresponding emotion 318.

The component emotion table 320 defines component emotion types in determined emotions and includes an entry identifier 322, a component emotion 324, a corresponding unfavorability level 326, and a corresponding binary encoding 328. The composite emotion table 330 specifies determined emotions made up of one or more component emotions. These determined emotions are also referred to herein as composite emotions. The composite emotion table 330 includes an entry identifier 332, a composite emotion 334, a corresponding unfavorability level 336, and a corresponding binary encoding 338. Depending on the embodiment, emotions exhibited by the calling user may be determined based on the component emotion table 320 and/or the composite emotion table 330. Although the binary encodings 328, 338 are shown as having encoding types of one-hot encoding and non-one-hot encoding, respectively, the encoding types can be tailored to suit the needs of a particular case; non-one-hot encoding can also be referred to as binary-type encoding.

In certain embodiments, each composite emotion conforms to a minimum count and/or a maximum count of component emotions, and the minimum count can be tailored to suit the needs of a particular case. For instance, in a particular embodiment where the minimum count is two and where the maximum count is also two, each composite emotion contains exactly a pair of component emotions. Depending on the embodiment, the pair of component emotions may be required to be distinct or otherwise may be permitted to be the same.

As shown in FIG. 3B, the frequency map 340 indicates, for each of the buttons 342 of a telephonic interface, a respective value from each of a lower frequency range 344 and a higher frequency range 346, under dual-tone multi-frequency signaling. The sequence table 350 includes an entry identifier 352, a key sequence 354, and a corresponding multi-frequency sequence 356. In some embodiments, the biometric mapping defines mappings between: part or all of the biometric table 310, and part or all of the component emotion table 320. In alternative embodiments, the biometric mapping defines mappings between: part or all of the biometric table 310, and part or all of the composite emotion table 330. Depending on the embodiment, part of a particular table can refer to only a portion of rows, fewer than all rows, of the particular table and/or only a portion of columns, fewer than all columns, of the particular table.

In one embodiment, the multi-frequency encoding scheme defines, based on the frequency map 340, mappings between: part or all of the component emotion table 320, and part or all of the sequence table 350. In an alternative embodiment, the multi-frequency encoding scheme defines, based on the frequency map 340, mappings: part or all of the composite emotion table 330, and part or all of the sequence table 350.

For instance, assuming that the client device 102 monitors a biometric aspect of the calling user and obtains a heart rate of one hundred and five beats per minute, while the calling user is on hold during a call to the call center for customer support. Based on information contained in the biometric table 310, the client device 102 determines that the heart rate is within the value range of one hundred and ten to one hundred and nineteen beats per minute, for a corresponding emotion of "disapproval." The client device 102 next determines, based on the component emotion table 320 and/or the composite emotion table 330, that the composite emotion of "disapproval" has a corresponding entry identifier of "5," a corresponding unfavorability level of "7," and a corresponding binary encoding of "0001 0000."

The unfavorability level of each composite emotion can be defined as any function of the unfavorability level of each component emotion of the respective composite emotion. For instance, the unfavorability level of a composite emotion can be a total of unfavorability levels of each component emotion of the composite emotion. Alternatively, the unfavorability level of a composite emotion can be a maximum value selected from the unfavorability levels of each component emotion of the composite emotion.

Still alternatively, the unfavorability level of a composite emotion can include a ceiling function of the total of unfavorability levels of each component emotion of the composite emotion, whereby ceiling function ensures that the unfavorability level of the composite emotion does not exceed a predefined value range, e.g., the value range of "0" to "10," with "10" representing the most unfavorable.

In one embodiment, the client device 102 then determines, based on the sequence table 350, that the composite emotion of "disapproval" has a corresponding key sequence of "5" on the telephonic interface and has a corresponding multi-frequency sequence of: a dual-tone signal of 770 hertz and 1336 hertz. Accordingly, the corresponding multi-frequency sequence can be transmitted to the call center application 104 in-band to convey the composite emotion of "disapproval" to the call center application 104. At least in some embodiments, any or all of the above mapping steps may be performed in forward or reverse order by the client device 102 and/or the call center application 104. Doing so permits forward mapping from biometric measurement to emotion to multi-frequency sequence and further permits backward mapping from multi-frequency sequence to emotion and to biometric measurement.

In some embodiments, a sequence of dual-tone signals can be transmitted based on predefined durations and/or delays specified by the multi-frequency encoding scheme. For instance, each dual-tone signal can be of a specified duration (e.g., 500 milliseconds), while each dual-tone signal is spaced apart from other dual-tone signals by a specified delay (e.g., 1 second). Further, in some embodiments, the frequency map 340 includes only the specific frequencies indicated as part of the lower frequency range 344 and the higher frequency range 346 and in effect defines permissible component values for each dual-tone signal. In other embodiments, the frequency map 340 can be expanded to include additional, arbitrarily defined frequencies in the lower frequency range and/or the higher frequency range, thereby providing a greater set of permissible component values for each dual-tone signal.

Figure 4:
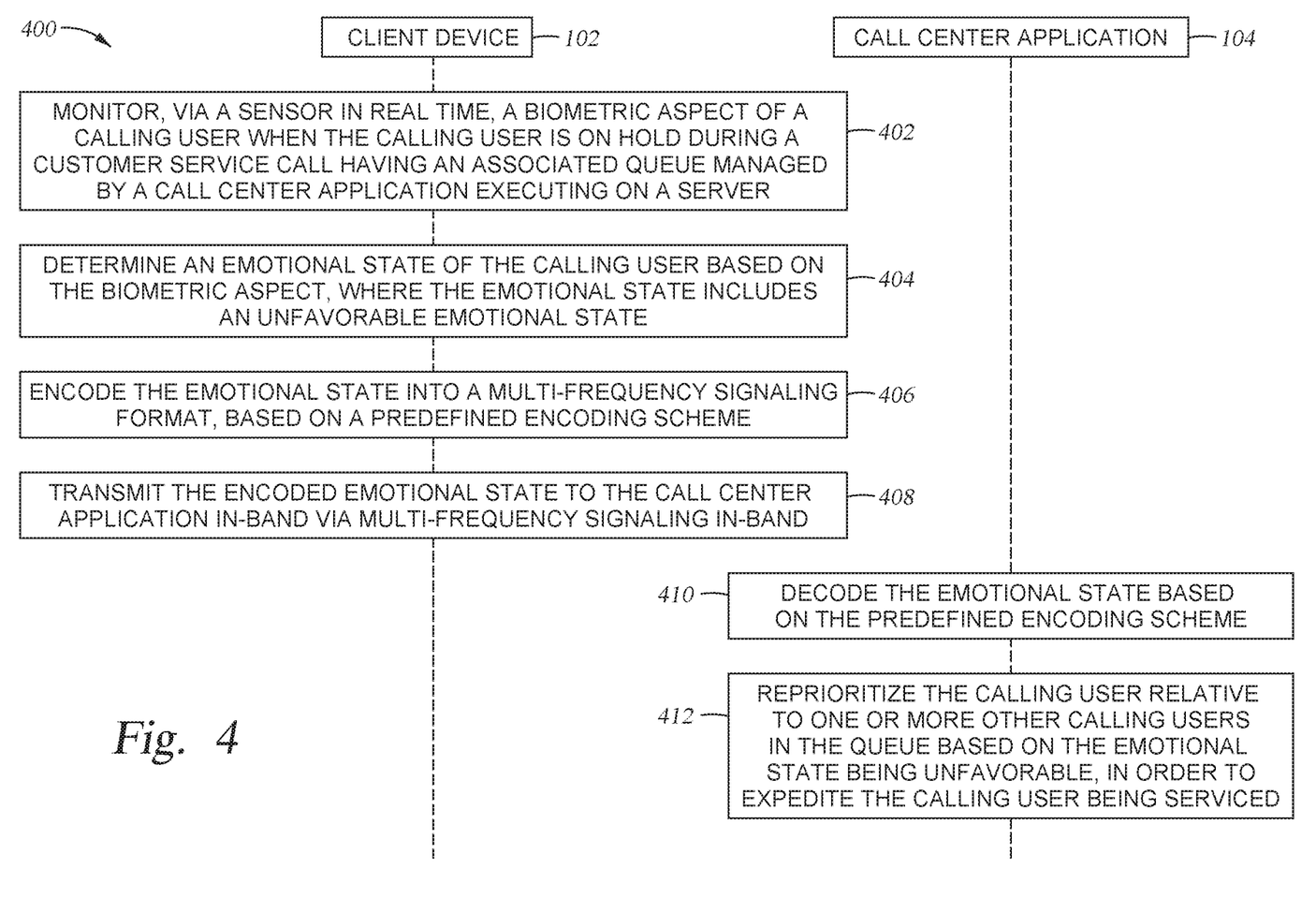
FIG. 4 is a flowchart depicting a method for reprioritizing waitlisted callers based on real-time biometric feedback, according to one embodiment presented in this disclosure.

FIG. 4 is a flowchart depicting a method 400 for reprioritizing waitlisted callers based on real-time biometric feedback, according to one embodiment presented in this disclosure. As shown, the method 400 begins at step 420, where the client device 102 monitors, via a sensor in real time, a biometric aspect of a calling user when the calling user is on hold during a customer service call having an associated queue that is managed by the call center application 102. In one embodiment, the queue is a waitlist of calling users currently on hold and awaiting availability of a customer support representative to discuss one or more concerns of the calling user. At step 404, the client device 102 determines an emotional state of the calling user, based on the biometric aspect, where the emotional state includes an unfavorable emotional state, such as a state of disapproval. At least in some embodiments, determining the emotional state of the calling user includes a digital output characterizing the emotional state of the calling user. The emotional state can include an emotional descriptor and/or an unfavorability level.

At step 406, the client device 102 encodes the emotional state into a multi-frequency signaling format, based on a predefined encoding scheme, such as a dual-tone multi-frequency encoding scheme. At step 408, the client device 102 transmits the encoded emotional state to the call center application 104 in-band via multi-frequency signaling. In some embodiments, the emotional state is transmitted based on computer telephony integration (CTI). The call center application 104 can execute on a server of a business of which the calling user is an affiliated party such as a customer, partner, vendor, supplier, etc. At step 410, the call center application 104 decodes the emotional state based on the predefined encoding scheme.

At step 412, the call center application 104 reprioritizes the calling user relative to one or more other calling users in the queue, based on the unfavorable emotional state, in order to expedite the calling user being serviced by a customer support representative. In a particular embodiment, the calling user is reprioritized by a reprioritizer module of the call center application. In some embodiments, upon determining that an emotional state of another calling user is not unfavorable, the other calling user is not reprioritized relative to the remaining users in the queue. After the step 412, the method 400 terminates.

In some embodiments, the emotional state of the user is determined based on a mapping table that defines mappings from biometric measurements to distinct emotional states. Additionally or alternatively, the emotional state is encoded based on an encoding scheme defined for encoding distinct emotional states into multi-frequency signals. The multi-frequency signaling can be dual-tone multi-frequency signaling (DTMF), and in some embodiments, the emotional state is transmitted in a manner inaudible to the calling user and/or the customer support representative. The encoding scheme can conform to a predefined document standard such as Voice Extensible Markup language (VoiceXML), in which case the encoded emotional state can be a VoiceXML snippet.

In one embodiment, the biometric aspect includes one or more of heart rate, body temperature, perspiration, hydration level, blood pressure, blood sugar, pupil dilation, and cortisol level. The emotional state is selected from a set of predefined emotional states that includes a selection of one or more of emotional state types. In a particular embodiment, the emotional state types include happiness, surprise, fear, sadness, disapproval, and anger.

In one embodiment, the conversation between the calling user and the customer support representative can address the concern of the calling user that caused the unfavorable emotional state in the first place. In such cases, the user can revert to a favorable emotional state at least as determined by the client device 102 via the one or more sensors. In some embodiments, a satisfaction rating for the customer support representative is automatically determined and assigned to the customer support representative based on the favorable emotional state. For instance, the satisfaction rating can be a function of one or more of a type and an extent of the favorable emotional state. Depending on the embodiment, the satisfaction rating for the customer support representative can be assigned to the customer support representative without requiring any intervention from the calling user or only upon receiving, from the calling user, input confirming or otherwise modifying the satisfaction rating. Doing so can streamline the rating of customer support representatives by calling users at least in some cases.

By reprioritizing waitlisted callers based on real-time biometric feedback according to the techniques disclosed herein, embodiments can manage the ordering of waitlisted callers in a manner that more accurately reflects the relative urgency or severity of the need of each waitlisted caller to be serviced by a customer support representative—at least relative to alternative approaches that either do not reprioritize waitlisted callers or that reprioritize waitlisted callers based on a criterion other than real-time biometric feedback. Doing so can improve the customer experience at least in some cases, and metrics such as customer loyalty, customer satisfaction, and/or customer retention can also be improved as a result.

Figure 5:
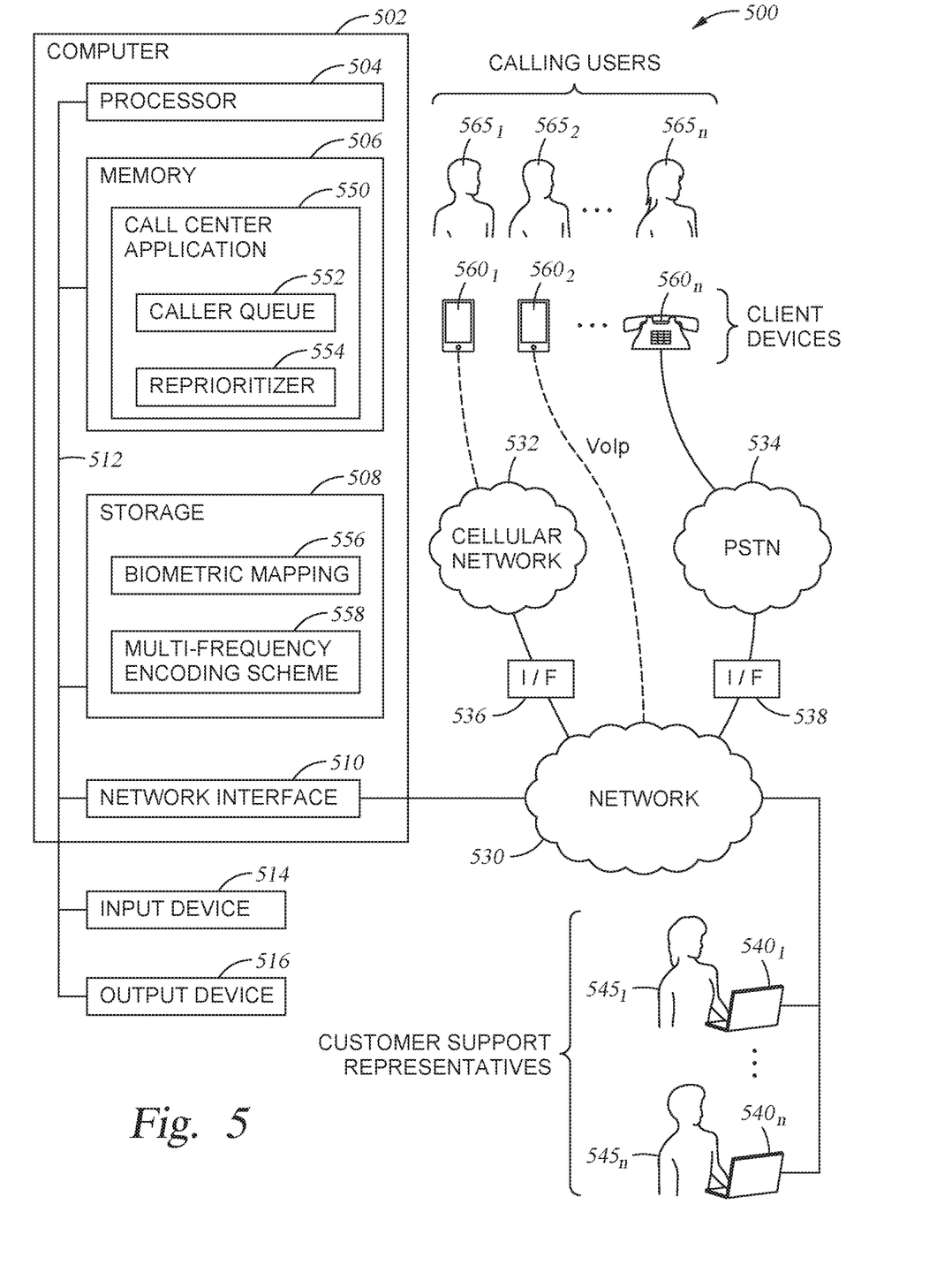
FIG. 5 is a block diagram illustrating hardware components of a system for reprioritizing waitlisted callers based on real-time biometric feedback, according to one embodiment presented in this disclosure.

FIG. 5 is a block diagram illustrating hardware components of a system 500 for reprioritizing waitlisted callers based on real-time biometric feedback, according to one embodiment presented in this disclosure. The system 500 includes a computer 502 configured to connect to other computers $540_{1-n}$ or devices of associated customer support representatives $545_{1-n}$ via a computer network 530. In general, the computer network 530 may be a telecommunications network and/or a wide area network (WAN). In a particular embodiment, the computer network 530 is the Internet. The computer 502 is further configured to connect to client computers or client devices $560_{1-n}$ of one or more associated calling users $565_{1-n}$.

As shown, the client devices $560_{1-n}$ include a client device $560_1$ operatively connected to the computer network 530 via a cellular network 532 and an interface 536 between the cellular network 532 and the computer network 530, where the client device $560_1$ initiates a call to the call center via cellular telephony. The client devices $560_{1-n}$ also include a client device $560_2$ operatively connected to the computer network 530 via a wireless access point in the computer network 530, where the client device $560_2$ initiates a call to the call center via Voice over Internet Protocol (VoIP).

The client devices $560_{1-n}$ further include a client device $560_n$ operatively connected to the computer network 530 via a public-switched telephone network 534, also referred to as a plain old telephone service, and the client device $560_n$ initiates a call to the call center via the public-switched telephone network and using a telephone device $560_n$ separate from a mobile device of the calling user, where the mobile device can be the client device $560_2$. In such instances, the mobile device can monitor biometric measurements of the user, determine an emotional state of the calling user, and transmit the emotional state via the computer network 530, while the calling user remains on hold with the call center via the telephone device $560_n$ of the calling user.

The computer 502 generally includes a processor 504 connected via a bus 512 to a memory 506, a network interface device 510, a storage 508, an input device 514, and an output device 516. The computer 502 is generally under the control of an operating system. Examples of operating systems include UNIX, versions of the Microsoft Windows® operating system, and distributions of the Linux® operating system. More generally, any operating system supporting the functions disclosed herein may be used. The processor 504 is included to be representative of a single CPU, multiple CPUs, a single CPU having multiple processing cores, and the like. Similarly, the memory 506 may be a random access memory. While the memory 506 is shown as a single identity, it should be understood that the memory 506 may comprise a plurality of modules, and that the memory 506 may exist at multiple levels, from high speed registers and caches to lower speed but larger DRAM chips. The network interface device 510 may be any type of network communications device allowing the computer 502 to communicate with the other computers $540_{1-n}$ via the network 530.

The storage 508 may be a persistent storage device. Although the storage 508 is shown as a single unit, the storage 508 may be a combination of fixed and/or removable storage devices, such as fixed disc drives, solid state drives, floppy disc drives, tape drives, removable memory cards or optical storage. The memory 506 and the storage 508 may be part of one virtual address space spanning multiple primary and secondary storage devices.

The input device 514 may be any device for providing input to the computer 502. For example, a keyboard and/or a mouse may be used. The output device 516 may be any device for providing output to a user of the computer 502. For example, the output device 516 may be any conventional display screen or set of speakers. Although shown separately from the input device 514, the output device 516 and input device 514 may be combined. For example, a display screen with an integrated touch-screen may be used.

As shown, the memory 506 of the computer 502 includes a call center application 550, which in turn includes a caller queue 552 and a reprioritizer module 554 per the embodiments disclosed herein. The storage 508 includes a biometric mapping 556 and a multi-frequency encoding scheme 558 per the embodiments disclosed herein. By reprioritizing waitlisted callers based on real-time biometric feedback according to the techniques presented herein, the ordering of waitlisted callers can at least in some cases be managed in a way that more accurately reflects the relative urgency or severity of the need of each waitlisted caller to be serviced by a customer support representative.

The descriptions of the various embodiments disclosed herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects presented in this disclosure may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or related data available in the cloud. For example, the call center application 550 could execute on a computing system in the cloud. Executing the call center application in the cloud permits customer support representatives to access functionality of the call center application from any computing system attached to a network connected to the cloud (e.g., the Internet) to service waitlisted callers that are reprioritized based on real-time biometric feedback according to the techniques disclosed herein.

While the foregoing is directed to embodiments presented in this disclosure, other and further embodiments may be devised without departing from the basic scope of contemplated embodiments, and the scope thereof is determined by the claims that follow.

What is claimed is:

1. A computer-implemented method of biometric monitoring to reprioritize calling users in a queue, the computer-implemented method comprising:
   accessing a predefined mapping table including mappings from biometric measurements to a plurality of distinct emotional states;
   accessing a predefined encoding scheme for encoding a plurality of distinct emotional states into a plurality of dual-tone multi-frequency signals;
   monitoring, via a sensor in real time, a biometric aspect of a calling user when the calling user is on hold during a customer service call having an associated queue, wherein the customer service call and the queue are managed by a server, wherein the sensor is associated with a client device of the user;
   generating, based on the biometric aspect of the calling user, a digital output characterizing an emotional state of the user, wherein the emotional state is determined based on the mappings and comprises an unfavorable emotional state;

encoding, based on the predefined encoding scheme and by one or more computer processors of the client device, the digital output characterizing the emotional state of the user, wherein the predefined encoding scheme conforms to a predefined digital document standard comprising Voice Extensible Markup Language, wherein the encoded emotional state comprises a Voice Extensible Markup Language snippet; and transmitting the encoded digital output to the server via dual-tone multi-frequency signaling, whereupon the server decodes the digital output and reprioritizes the calling user relative to other calling users in the queue based on the unfavorable emotional state, in order to expedite the calling user being serviced.

2. The computer-implemented method of claim 1, wherein the biometric aspect is selected from heart rate, body temperature, perspiration, hydration level, blood pressure, blood sugar, pupil dilation, and cortisol level.

3. The computer-implemented method of claim 2, wherein the encoded digital output is transmitted to the server in a manner inaudible to the calling user, wherein the server comprises a server of a business of which the calling user is a customer.

4. The computer-implemented method of claim 3, wherein the emotional state is selected from a plurality of predefined emotional states including happiness, surprise, fear, sadness, disapproval, and anger, wherein a subset of the plurality of predefined emotional states is designated as unfavorable.

5. The computer-implemented method of claim 4, wherein a plurality of biometric aspects of the calling user, including the biometric aspect, is determined, the plurality of biometric aspects including each biometric aspect selected from heart rate, body temperature, perspiration, hydration level, blood pressure, blood sugar, pupil dilation, and cortisol level, wherein the emotional state of the user is determined based on the plurality of biometric aspects.

6. The computer-implemented method of claim 5, wherein the calling user is serviced by a customer support representative of the business, wherein servicing of the calling user addresses a concern of the calling user that caused the emotional state, whereafter the calling user reverts to a favorable emotional state;
wherein the favorable emotional state is determined based on monitoring a second biometric aspect of the calling user during or subsequent to the servicing, wherein a satisfaction rating for servicing the calling user is automatically determined and assigned to the customer support representative based on the favorable emotional state.

7. The computer-implemented method of claim 6, wherein the calling user comprises a first calling user, where the other calling users in the queue include a second calling user, wherein upon determining that an emotional state of the second calling user is not unfavorable, the second calling user is not reprioritized relative to other users in the queue, wherein the queue comprises a waitlist;
wherein the server comprises a call center application, wherein the emotional state is selected from an emotional descriptor and an unfavorability level.

8. The computer-implemented method of claim 1, wherein the encoded digital output is transmitted to the server in a manner inaudible to the calling user.

9. The computer-implemented method of claim 1, wherein the emotional state is selected from a plurality of predefined emotional states including happiness, surprise, fear, sadness, disapproval, and anger.

10. The computer-implemented method of claim 9, wherein a subset of the plurality of predefined emotional states is designated as unfavorable.

11. A computer program product of biometric monitoring to reprioritize calling users in a queue, the computer program product comprising:
a computer-readable storage medium having computer readable program code embodied therewith, the computer readable program code executable by one or more computer processors to perform an operation comprising:
accessing a predefined mapping table including mappings from biometric measurements to a plurality of distinct emotional states;
accessing a predefined encoding scheme for encoding a plurality of distinct emotional states into a plurality of dual-tone multi-frequency signals;
monitoring, via a sensor in real time, a biometric aspect of a calling user when the calling user is on hold during a customer service call having an associated queue, wherein the customer service call and the queue are managed by a server, wherein the sensor is associated with a client device of the user;
generating, based on the biometric aspect of the calling user, a digital output characterizing an emotional state of the user, wherein the emotional state is determined based on the mappings and comprises an unfavorable emotional state;
encoding, based on the predefined encoding scheme, the digital output characterizing the emotional state of the user, wherein the predefined encoding scheme conforms to a predefined digital document standard comprising Voice Extensible Markup Language, wherein the encoded emotional state comprises a Voice Extensible Markup Language snippet; and
transmitting the encoded digital output to the server via dual-tone multi-frequency signaling, whereupon the server decodes the digital output and reprioritizes the calling user relative to other calling users in the queue based on the unfavorable emotional state, in order to expedite the calling user being serviced.

12. The computer program product of claim 11, wherein the biometric aspect is selected from heart rate, body temperature, perspiration, hydration level, blood pressure, blood sugar, pupil dilation, and cortisol level.

13. The computer program product of claim 11, wherein the encoded digital output is transmitted to the server in a manner inaudible to the calling user.

14. The computer program product of claim 11, wherein the emotional state is selected from a plurality of predefined emotional states including happiness, surprise, fear, sadness, disapproval, and anger.

15. The computer program product of claim 14, wherein a subset of the plurality of predefined emotional states is designated as unfavorable.

16. A client device of biometric monitoring to reprioritize calling users in a queue, the client device comprising:
one or more computer processors; and
a memory containing a program which, when executed by one or more computer processors, performs an operation comprising:
accessing a predefined mapping table including mappings from biometric measurements to a plurality of distinct emotional states;
accessing a predefined encoding scheme for encoding a plurality of distinct emotional states into a plurality of dual-tone multi-frequency signals;

monitoring, via a sensor in real time, a biometric aspect of a calling user when the calling user is on hold during a customer service call having an associated queue, wherein the customer service call and the queue are managed by a server, wherein the sensor is associated with the client device;

generating, based on the biometric aspect of the calling user, a digital output characterizing an emotional state of the user, wherein the emotional state is determined based on the mappings and comprises an unfavorable emotional state;

encoding, based on the predefined encoding scheme, the digital output characterizing the emotional state of the user, wherein the predefined encoding scheme conforms to a predefined digital document standard comprising Voice Extensible Markup Language, wherein the encoded emotional state comprises a Voice Extensible Markup Language snippet; and transmitting the encoded digital output to the server via dual-tone multi-frequency signaling, whereupon the server decodes the digital output and reprioritizes the calling user relative to other calling users in the queue based on the unfavorable emotional state, in order to expedite the calling user being serviced.

17. The client device of claim 16, wherein the biometric aspect is selected from heart rate, body temperature, perspiration, hydration level, blood pressure, blood sugar, pupil dilation, and cortisol level.

18. The client device of claim 16, wherein the encoded digital output is transmitted to the server in a manner inaudible to the calling user.

19. The client device of claim 16, wherein the emotional state is selected from a plurality of predefined emotional states including happiness, surprise, fear, sadness, disapproval, and anger.

20. The client device of claim 19, wherein a subset of the plurality of predefined emotional states is designated as unfavorable.

* * * * *